US 6,558,311 B1

(12) United States Patent
Muntermann

(10) Patent No.: US 6,558,311 B1
(45) Date of Patent: May 6, 2003

(54) DEVICE FOR TREATMENT WITH MAGNETIC FIELDS

(76) Inventor: Axel Muntermann, Gotenweg 51, D-35578 Wetzlar (DE)

(*) Notice: Subject to any disclaimer, the term of this patent is extended or adjusted under 35 U.S.C. 154(b) by 0 days.

(21) Appl. No.: 09/720,464

(22) PCT Filed: Jun. 6, 1999

(86) PCT No.: PCT/DE99/01722

§ 371 (c)(1), (2), (4) Date: Dec. 21, 2000

(87) PCT Pub. No.: WO99/66986

PCT Pub. Date: Dec. 29, 1999

(30) Foreign Application Priority Data

Jun. 22, 1998 (DE) .......................... 198 27 736

(51) Int. Cl.7 ................................................ A61N 1/00
(52) U.S. Cl. ....................................................... 600/13
(58) Field of Search ................. 600/411, 407, 600/13; 424/9.3; 335/306; 324/309

(56) References Cited

U.S. PATENT DOCUMENTS

| 4,428,366 A | | 1/1984 | Findl et al. |
| 5,050,605 A | | 9/1991 | Eydelman et al. |
| 5,186,924 A | * | 2/1993 | Fishman ................ 424/9.3 |
| 5,224,922 A | | 7/1993 | Kurtz |
| 5,365,172 A | * | 11/1994 | Hrovat et al. ............ 324/309 |
| 5,366,435 A | * | 11/1994 | Jacobson .................... 600/13 |
| 5,690,109 A | * | 11/1997 | Govind et al. ............ 600/411 |
| 5,769,787 A | * | 6/1998 | Lemelson ................. 600/407 |
| 5,880,661 A | * | 3/1999 | Davidson et al. ......... 335/306 |

FOREIGN PATENT DOCUMENTS

| DE | 28 21 114 A1 | 11/1978 | ............ A61N/1/42 |
| DE | 40 26 173 A1 | 2/1991 | ............ A61N/2/04 |
| WO | WO 97/46277 | 11/1997 | ............ A61N/2/02 |

* cited by examiner

Primary Examiner—Eric F. Winakur
Assistant Examiner—Nikita Veniaminov

(57) ABSTRACT

An apparatus for treatment of a portion of a biological body with magnetic fields having a device adapted for producing spin resonances for treatment within a portion of the biological body to be treated. The apparatus includes a magnet for producing a magnetic field, a coil system for producing a magnetic alternating field at right angles to the magnetic field, control electronics for actuation of the magnet and the coil system adapted to produce nuclear spin resonance in at least a portion of a biological body, and a device for repeated actuation of the control electronics to produce a defined sequence of nuclear spin resonances. The sequence of nuclear spin resonances produced by the device is determined by the spin-lattice relaxation time $T_1$ of at least one portion of the biological body, and has a repetition rate of approximately $3T_1$.

8 Claims, 3 Drawing Sheets

DEVICE FOR TREATMENT WITH MAGNETIC FIELDS

The invention relates to the treatment of at least a portion of a biological body with magnetic fields and to an apparatus for treatment with magnetic fields.

Apparatuses are known which use pulsed or modulated magnetic fields to produce a positive influence on biological tissue. In this case, as can be found, for example, in DE 40 26 173, the tissue is subjected to a constant magnetic field and to a magnetic alternating field superimposed on it. During use of such appliances, it has been possible to show that a positive therapeutic effect can be achieved by subjecting biological tissue to magnetic fields and/or to magnetic alternating fields. The healing affect of such magnetic-field therapy appliances covers, inter alia, the alleviation of osteoporosis or the consequences of a stroke. In this case, it appears probable that the magnetic fields which are applied promote transport and/or metabolic processes which lead to a positive therapeutic effect. Until now, it has been assumed that the process described above is caused by the stimulation and/or the absorption of ion cyclotron resonances (ICR) in a biological body. However, in some circumstances, this appears to be questionable since cyclotron resonances in general occur only in free particles, for example in a vacuum or in the case of electrons in the conduction band of a semiconductor. Furthermore, a simple calculation can also be used to show that a cyclotron movement would take place on a circular path whose radius is actually greater than the average diameter of a cross section of a human body. This means that an explanation of the energy transfer based on cyclotron resonance may be questionable, particularly in the case of solid tissue. In practice, it has been found that, with the existing magnetic-field therapy appliances, it is often necessary to carry out a number of treatments initially in order in this way to define the frequencies for the subsequent treatments which cause the desired positive effect. This procedure means that therapy with magnetic fields is very complex and imprecise and only exceptionally, if at all, allows a deliberate procedure for complaints, which can be defined and located, in solid or liquid material.

The invention is thus based on the object of providing an apparatus for treatment with magnetic fields, which avoids the said disadvantages and which, in particular, for the first time allows treatments with magnetic fields to be carried out in all biological materials in a specific and reproducible manner, irrespective of whether any ionic particles are present.

This object is achieved in a very highly surprising manner just by the features of claim 1. Advantageous and preferred developments are the subject matter of the dependent claims.

In comparison to known solution attempts, the apparatus according to the invention is based on the idea that the positive treatment effect can be achieved by producing repeated spin resonance sequences.

One preferred embodiment of the invention comprises, in a particularly advantageous manner, a magnet for producing an essentially constant magnetic field, and a coil system for producing a magnetic alternating field at right angles to the magnetic field of the magnet, with this, in a manner which is obvious to a person skilled in the art, corresponding to a classical arrangement for carrying out spin resonance. Furthermore, an advantageous development of the apparatus according to the invention also has control electronics for actuation of the magnet and the coil system, which control electronics can be adjusted such that nuclear spin resonance is produced in a biological body introduced between the magnets described above. In this case, in a highly advantageous manner, the control device has an associated device by means of which parameters or intervals can be defined over a fixed treatment time period, based on which the apparatus according to the invention repeats the nuclear spin resonance process or nuclear spin absorption process controlled by the control electronics.

In the context of the invention, it has been found to be very highly advantageous if the repetition rate, that is to say the time sequence of the nuclear spin resonance is carried out, is determined as a function of the spin-lattice relaxation time $T_1$. The spin-lattice relaxation time describes, in the form of a time constant, the exponential or logarithmic build-up of macroscopic magnetization in the direction of a magnetic field. The resonant injection of a magnetic alternating field at right angles to the said magnetic field reduces the magnetization in the direction of the magnetic field. If the resonant injection is stopped after this decrease in the magnetization, then the magnetization in the magnetic field direction builds up once again, in which case it can be assumed on the basis of the logarithmic growth that the magnetization reaches approximately 95% of the initial value of the magnetization once again after a time of approximately $3T_1$. This means that, after a time interval of $3T_1$, a new effective energy transfer can be achieved by spin resonance. The definition of the spin resonance repetition rate to be three times the spin-lattice relaxation time of the body or body part to be treated is thus ideally typical for the subject matter of the present invention, but is not essential, so that other frequencies are also feasible. Furthermore, this definition allows a positive biological effect to be achieved immediately. In contrast to the prior art, it is no longer necessary to carry out a number of comprehensive initial treatments to determine, more or less objectively, the frequency which achieves a biological effect. Since the spin resonance can be used both for gaseous molecules and for molecules which are in solution and for molecules which are incorporated in solid form, the corresponding spin-lattice relaxation times, or those required for the treatment, are also advantageously accessible by measurements.

In consequence, in a further development of the invention, the apparatus for treatment with magnetic fields comprises a further coil system. The axis of this coil system is preferably at right angles to both the axis of the magnet and the axis of the first coil system. In one preferred embodiment, this coil system is used as a detection coil system. In this case, before the start of the treatment, the spin-lattice relaxation time $T_1$ can be determined in a very highly advantageous manner using the detection coils, for example in the course of a spin-echo measurement, and, as already described above, this allows the repetition rate to be defined.

Furthermore, in a positive further refinement of the subject matter of the invention, this subject matter has an associated evaluation device which allows the required parameter $T_1$ to be determined from the spin-echo measurement described above. If, furthermore, the already described detection coil is also provided, then the repetition rate for the spin resonance can be obtained directly and entirely objectively, locally, for the body to be treated or body part to be treated. This means that there is no longer any need for treatment appointments which serve only to find a possible "effective frequency". However, in a simplified embodiment in this case, this device can also advantageously be used just to record and to provide already defined values, or values which can be found in the references, for $T_1$ or for other parameters such as the magnetic field $B_0$, the alternating field $B_1$, the Larmor frequency $f_0$ or other appropriate parameters, in order in this way to define the conditions in which the treatment can be carried out by means of spin resonance.

It is also very highly advantageous if the control electronics comprise a measurement device which is able to use, for example, installed detection coils such as those already described above to measure the energy which is emitted to the tissue or the body part to be treated in the course of a sequence of nuclear spin resonances. This thus allows a relationship to be produced in a very simple way, using which it is possible to represent the relationship between the treatment success and the "energy dose" emitted to the body. Appropriate recording can, in particular, be used to define specific "energy doses" for a specific application. Furthermore, alternatively, it is possible to use this for monitoring the progress of the illness. In this case, it is obvious to a person skilled in the art that such recordings can also be used in a very wide number of different ways.

In an ideal situation, it is sufficient for the spin resonance to inject a discrete frequency, namely the so-called Larmor frequency, of an alternating field in order, in the classical sense, to tilt the macroscopic magnetization or to achieve a corresponding energetic transfer. In practice, no such discrete frequency can be found. In addition, it must be expected that the magnetic field being applied is not homogeneous and that chemical shifts also result in inhomogeneities within the areas which are being treated with spin resonance so that the spins do not precess in phase at a standard Larmor frequency. In order, nevertheless, to cause as many spins as possible to be tilted, the magnetic alternating field produced by the coil system according to the invention advantageously comprises a large number of defined Fourier components.

In a positive development of the apparatus according to the invention, the magnet comprises a Helmholtz coil arrangement. Helmholtz coils are distinguished in particular by being able to produce essentially constant homogeneous magnetic fields. Furthermore, they offer the advantage that they allow field shifting to be carried out in a simple manner. This field shifting can be carried out firstly by varying the current flowing through the coils, or secondly by superimposing an additional magnetic field on the Helmholtz field by means of a further coil. A pair of Helmholtz coils thus make it simple to carry out nuclear spin resonance by field shifting.

However, in practice, it has been possible to show in a very highly advantageous development of the invention that there is no need for a Helmholtz coil arrangement such as that described above. For example, when spin resonance is being carried out for treatment purposes, it is sufficient to use a hard-ferrite magnet to produce the magnetic field. Since simple magnets can also be used, this allows the apparatus according to the invention to be produced in a considerably more advantageous manner, thus allowing the treatment with the apparatus according to the invention to be available to a large range of patients. In this context, it has advantageously been possible to show that, with magnetic field strengths of approximately 22 Gauss, a field discrepancy of up to approximately ±0.6 Gauss is sufficient for treatment purposes with the present invention.

This is feasible, inter alia, by superimposing an additional variable auxiliary field, by means of an auxiliary coil, on the comparatively severely fluctuating field. In this case, this auxiliary coil is actuated by a control device in such a way that the nuclear spin resonance takes place using a rapid adiabatic run procedure with a magnetic alternating field injected at a constant frequency. The adiabatic run is based, inter alia, on shifting the field of the magnetic field produced by the magnet. In this case, in one possible embodiment, the magnetic field of the magnet first of all has the magnetic field from an auxiliary coil superimposed on it additively, that is to say amplifying it, and, at the end of a resonance sequence, has the said magnetic field superimposed on it in a compensating manner, that is to say attenuating it. This means that the magnetic field of the magnet is reduced continuously during a resonance sequence. The magnetic field is preferably reduced in the form of a sawtooth. In the adiabatic run, however, it is necessary to ensure that the field variation is not carried out too quickly. Specifically, if one considers the magnetic fields and the magnetization in the reference system rotating at the Larmor frequency, then it is evident that the field superimposition within this rotating reference system results in a further Larmor movement of additional magnetization, which is superimposed on the original movement produced by the magnetic field. The field variation results in this additional magnetization changing its direction in the rotating reference system, since it is aligned with the magnetic field resulting from the superimposition. However, in this case, this takes place without any energy transfer, that is to say adiabatically, only if the variation in the magnetic field takes place sufficiently slowly. In this way, in a highly advantageous and cost-effective manner, it is possible for the spin resonance to reach all the body parts located in the active zone and to achieve an essentially optimized energy exchange, since, as a result of the shifting of the magnetic field and despite any possible discrepancy in the field density, the spins are subjected to a suitable magnetic field so that resonance can in any case occur at the transversely injected Larmor frequency.

Furthermore, it is within the scope of the invention to carry out the spin resonance not only, as described above, by field shifting but also to do this by pure frequency shifting, or to allow the energy transfer of the spin resonance to take place by means of combined field/frequency shifting. Although this does not preclude a rapid adiabatic run.

The invention will be described in detail in the following text using preferred embodiments and with reference to the attached drawing, in which.

Figure 1:
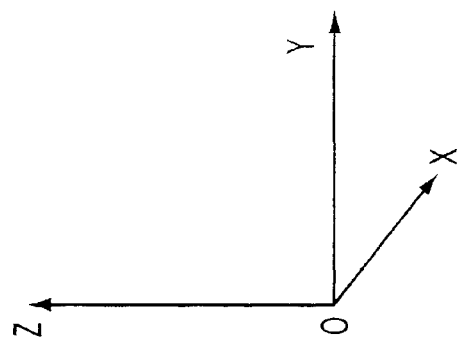
FIG. 1 shows a perspective illustration of one possible arrangement of magnetic fields and coils according to the invention.
Figure 1:
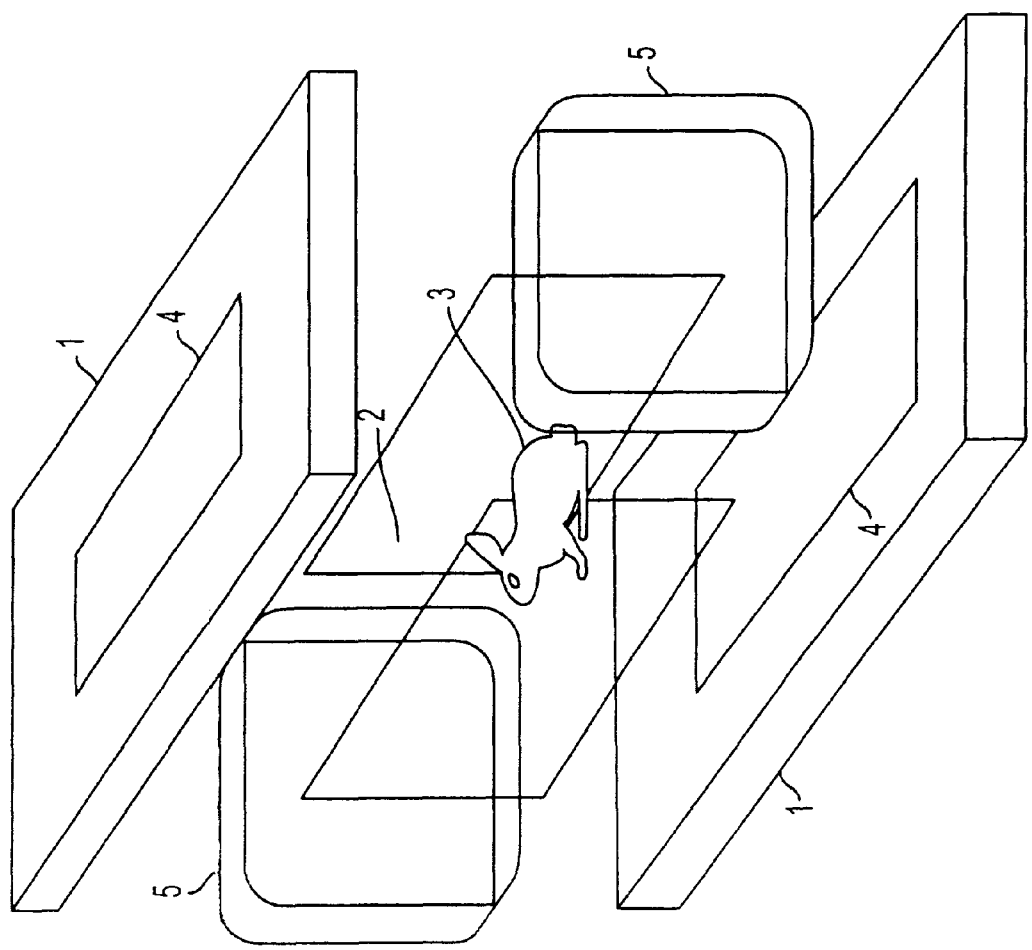

FIG. 1 shows a schematic illustration of one preferred arrangement of coils and magnets for an apparatus according to the invention. The coordinate system shown to the right of the arrangement is intended to indicate the physical position of the individual coils. In this case, two poles of a permanent magnet 1 are arranged at right angles to the z-axis, that is to say at right angles to the vertical. The lines of force of the magnetic field produced by the permanent magnet run parallel to the z-axis. The two poles 1 of the magnet are separated from one another and thus form an intermediate space 2. The intermediate space is the so-called active area 2 in which the magnetic fields and the spin resonance which is carried out produce their effect on the biological body 3. The permanent magnet 1 preferably produces a magnetic field of $B_0 = 22$ Gauss, in which case a field density discrepancy of approximately ±0.5 Gauss can be tolerated with respect to the field density in the course of the rapid adiabatic run. FIG. 1 also shows that there is an auxiliary coil 4 associated with the permanent magnet 1. When carrying out spin resonance, the auxiliary coil 4 is used to superimpose a varying magnetic field on the essentially constant magnetic field, in order to shift the field in the course of the adiabatic run. A transmitting coil system 5 is arranged at right angles to the z-axis and at right angles to the lines of force of the permanent magnet, that is to say along the x-axis. The transmitting coils 5 produce a magnetic alternating field. During an adiabatic run, this alternating field is set to an essentially fixed Larmor frequency of a biological body to be treated. If required, as shown in FIG. 1, a further coil system 6 may also be used. This coil system 6 can be used firstly in the course, for example, of spin-echo measurements to determine the spin-lattice relaxation time $T_1$ of the biological body to be treated, and can secondly also be used to determine the energy which is emitted by a sequence of spin resonances to the biological object in the active zone 2.

Figure 2:
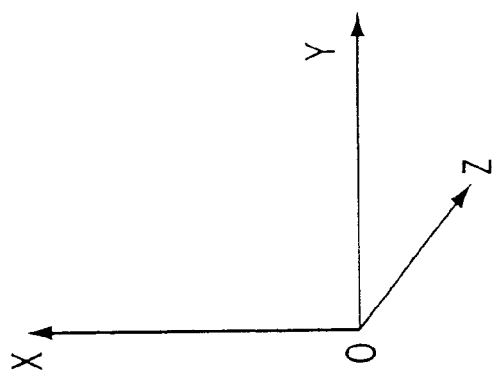
FIG. 2 shows a perspective illustration of a further arrangement of magnetic fields and coils according to the invention.
Figure 2:
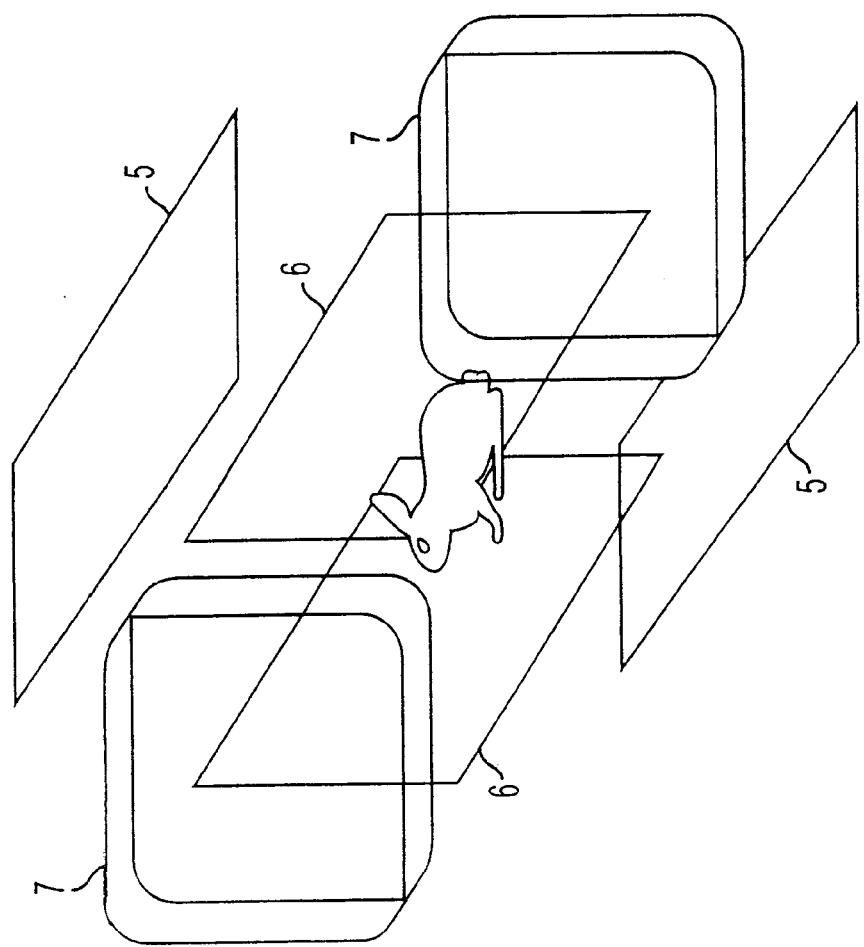

FIG. 2 shows a further preferred coil or magnetic field arrangement of the apparatus according to the invention. In comparison to FIG. 1, the magnetic field $B_0$ is not produced by a permanent magnet 1, but by a pair of Helmholtz coils 7. The use of Helmholtz coils for this embodiment means that there is no need for the auxiliary coil 4 shown in FIG. 1. The field shifting to be carried out in the course of any possible rapid adiabatic run can be achieved by suitable variation of the coil current.

Figure 3:
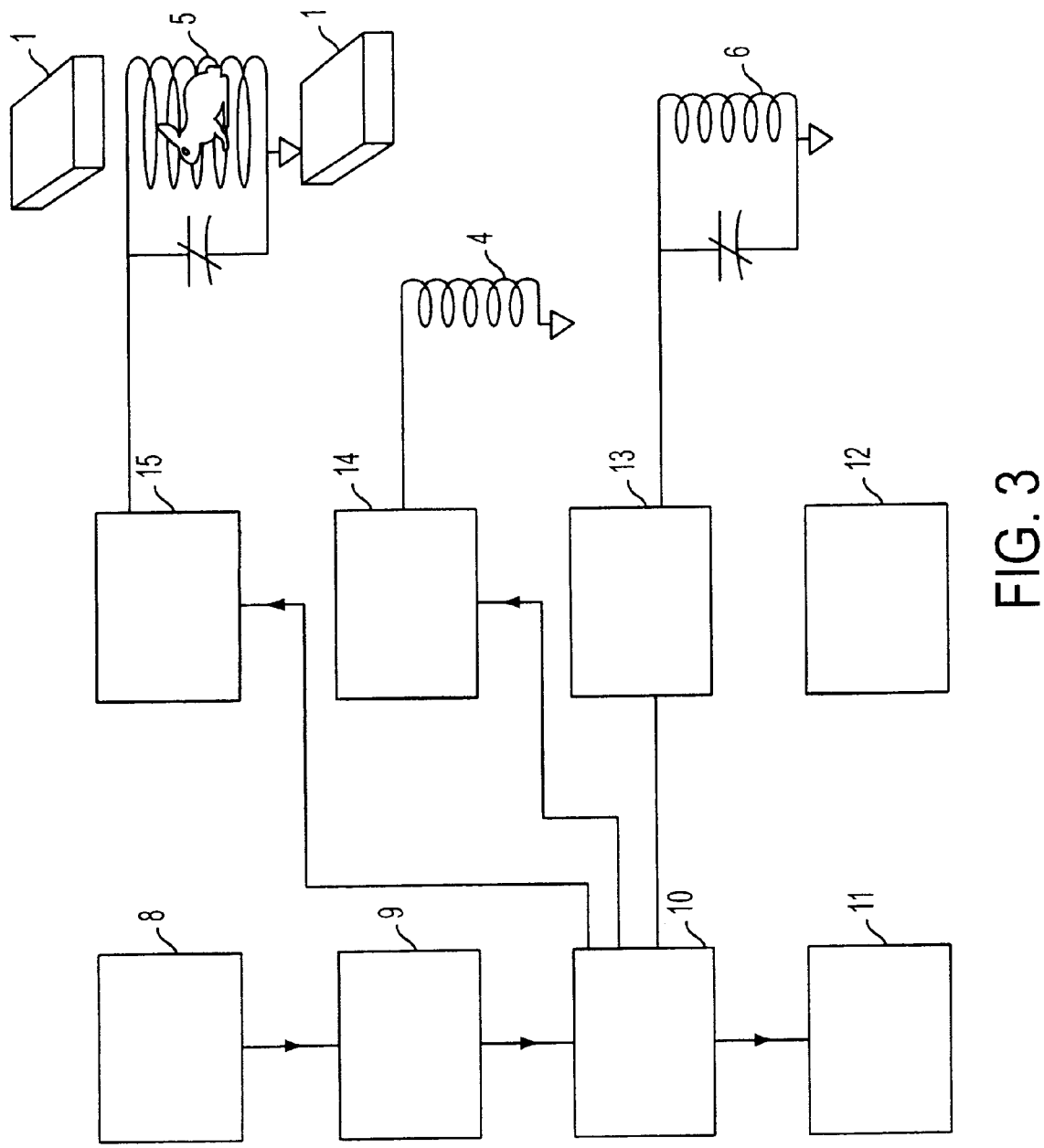
FIG. 3 shows a block diagram, schematically illustrating the functional groups when using an apparatus according to the invention for treatment with magnetic fields.

FIG. 3 shows a block diagram which illustrates schematically the functional groups of a treatment apparatus in which, by way of example, an apparatus according to the invention is used for treatment with magnetic fields. In this exemplary embodiment, the apparatus comprises a so-called card reader 8, which is suitable for recording and for identifying smart cards equipped with magnetic strips and/or memory chips which can be written to, such as those which are nowadays normally already issued, for example, to the patients by the medical insurance companies. The present apparatus is thus able to record information about patients and relating to patient treatment automatically, and to carry out further processing in the context of the apparatus according to the invention. Such data may, inter alia, comprise a history of the previous treatments carried out, details about the treatment duration, the number of treatments ordered or paid for, individual details relating to the treatment intensity and, and this is highly important, the repetition rate at which the application of spin resonance is intended to be carried out. In this case, a person skilled in the art and who is active in this field will easily see that the described data transmission and access authorization can also be carried out in some other form. In consequence, for example, transmission from a central point is also possible, by means of suitable interfaces with which a person skilled in the art will be familiar.

The data which have been read are then passed to a microcontroller 9, which also includes all the control devices. The microprocessor device controls, inter alia, the spin resonance process, the repetition rate and the sequence of a number of spin absorption processes, and their effectiveness. Furthermore, the forward movement of a treatment couch within the active zone 2 (FIG. 1) of the apparatus according to the invention can also be controlled by the said microcontroller device 9 when a number of body parts are being treated or a body area is being treated by means of the device, for example. By way of example, FIG. 3 shows the link between the microcontroller and the function generator 10 according to the invention. The function generator 10 uses appropriate tuned circuits to produce, inter alia, suitable frequencies for defined production of nuclear spin resonances, which are controlled and monitored by the microcontroller device. Furthermore, the apparatus according to the invention includes a display 11 which, for example, allows the patient or a supervisor to monitor the nuclear spin resonance treatment process in detail.

What is claimed is:

1. A method for treatment of a portion of a biological body with a magnetic field, comprising the following method steps;

a) determining a repetition rate for a sequence of nuclear spin resonances, b) executing a sequence of nuclear spin resonances within said biological body based on the determined repetition rate for treatment of said biological body.

2. The method as claimed in claim 1, comprising determining the repetition rate by the spin-lattice relaxation time $T_1$.

3. The method as claimed in claim 2 comprising obtaining the spin-lattice relaxation time $T_1$ by spin-echo measurement or from existing data records.

4. The method as claimed in claim 1, wherein the repetition rate has a value of approximately $3T_1$, whereby $T_1$ is the relaxation time.

5. The method as claimed in claim 1, wherein the nuclear spin resonance takes place in a rapid adiabatic run.

6. The method as claimed in claim 1, wherein the nuclear spin resonance takes place via a device for field shifting.

7. The method as claimed in claim 1, wherein the nuclear spin resonance takes place via a device for modulation frequency shifting.

8. The method as claimed in claim 1, wherein the nuclear spin resonance takes place via a device for combined field/frequency shifting.

* * * * *